(12) United States Patent
Wille et al.

(10) Patent No.: US 7,420,162 B2
(45) Date of Patent: Sep. 2, 2008

(54) SYSTEMS AND METHODS FOR CREATING STABLE CAMERA OPTICS

(75) Inventors: Steven Lewis Wille, Palantine, IL (US); Anthony P. DelMedico, Niles, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 310 days.

(21) Appl. No.: 11/158,640

(22) Filed: Jun. 22, 2005

(65) Prior Publication Data

US 2006/0002518 A1 Jan. 5, 2006

Related U.S. Application Data

(60) Provisional application No. 60/584,019, filed on Jun. 30, 2004.

(51) Int. Cl.
*G01D 18/00* (2006.01)
(52) U.S. Cl. .................................. 250/300; 250/370.11
(58) Field of Classification Search ............ 250/227.25, 250/227.24, 300, 370.11, 390.11
See application file for complete search history.

(56) References Cited

U.S. PATENT DOCUMENTS

| | | | | |
|---|---|---|---|---|
| 4,122,246 A | * | 10/1978 | Sierawski | 528/15 |
| 4,533,489 A | * | 8/1985 | Utts et al. | 252/301.17 |
| 4,543,485 A | * | 9/1985 | Ishii et al. | 250/487.1 |
| 5,059,798 A | * | 10/1991 | Persyk | 250/363.03 |
| 5,061,855 A | * | 10/1991 | Ryuo et al. | 250/361 R |
| 5,153,438 A | * | 10/1992 | Kingsley et al. | 250/370.09 |
| 6,300,624 B1 | * | 10/2001 | Yoo et al. | 250/254 |
| 6,369,390 B1 | * | 4/2002 | Genna | 250/368 |
| 6,452,185 B1 | * | 9/2002 | Weisenberger et al. | 250/370.11 |
| 2002/0102077 A1 | * | 8/2002 | Szum et al. | 385/100 |
| 2003/0025449 A1 | * | 2/2003 | Rossner | 313/512 |
| 2005/0104000 A1 | * | 5/2005 | Kindem et al. | 250/361 R |
| 2005/0250903 A1 | * | 11/2005 | Tanaka et al. | 524/861 |

* cited by examiner

*Primary Examiner*—David P. Porta
*Assistant Examiner*—Djura Malevic
(74) *Attorney, Agent, or Firm*—Peter L. Kendall

(57) ABSTRACT

In some preferred embodiments, a medical imaging system having stable camera optics is provided that includes: a photon emitting source that emits photons towards a plurality of photon receivers; an optical interface between said photon emitting source and said plurality of photon receivers including an optical coupling gel that is prone to discoloration from local contaminants and an optical coating adjacent said optical coupling gel; and said optical coating having means for avoiding discoloration of said optical coupling gel.

18 Claims, 3 Drawing Sheets

SYSTEMS AND METHODS FOR CREATING STABLE CAMERA OPTICS

BACKGROUND

1. Field of the Invention

The present invention relates generally to imaging systems and, more particularly, to systems and methods for creating stable camera optics. In addition, the preferred embodiments provide a system and method for creating stable optics in medical imaging systems having optical couplings prone to discoloration by local contaminants.

2. Discussion of the Background

A variety of medical imaging systems are known. Some illustrative imaging systems include nuclear medical imaging systems (e.g., gamma cameras), computed tomography (CT or CAT) systems, magnetic resonance imaging (MRI) systems, positron-emission tomography (PET) systems, ultrasound systems and/or the like.

With respect to nuclear medical imaging systems, nuclear medicine is a unique medical specialty wherein radiation (e.g., gamma radiation) is used to acquire images that show, e.g., the function and/or anatomy of organs, bones and/or tissues of the body. Typically, radioactive compounds, called radiopharmaceuticals or tracers, are introduced into the body, either by injection or ingestion, and are attracted to specific organs, bones or tissues of interest. These radiopharmaceuticals produce gamma photon emissions that emanate from the body and are captured by a scintillation crystal, with which the photons interact to produce flashes of light or "events." These events can be detected by, e.g., an array of photodetectors, such as photomultiplier tubes, and their spatial locations or positions can be calculated and stored. In this manner, an image of an organ, tissue or the like under study can be created from the detection of the distribution of the radioisotopes in the body.

A number of illustrative imaging systems are shown in the following United States Patents and Publications, the entireties of which are incorporated herein by reference: (1) U.S. Pat. No. 5,059,798, issued on Oct. 22, 1991, entitled Frangible Bonding of Photomultiplier Tubes for Use In Scintillation Cameras and PET Scanners, listed as assigned to Siemens Gammasonics, Inc.; (2) U.S. Pat. No. 4,605,856, issued on Aug. 12, 1986, entitled Method and Device for Stabilizing Photomultiplier Tubes of Radiation Imaging Device Against Drift, also listed as assigned to Siemens Gammasonics, Inc.; (3) U.S. Pat. No. 4,574,478, issued on Mar. 11, 1986, entitled Method and Device for Demounting In a Radiation Detector a Photomultiplier Tube; (4) U.S. Published Patent Application No. 20040036026, published on Feb. 26, 2004, and filed on Aug. 21, 2002, naming inventors J. Engdahl, et al., and entitled System and Method for Calibrating and Tuning a Gamma Camera, assigned to the present assignee; and (5) U.S. Published Patent Application No. 20030034455A1, published on Feb. 20, 2003, entitled Scintillation Detector System and Method Providing Energy and Position Information, filed on Apr. 3, 2002, which states, inter alia, in paragraph [0099]:

"A preferred reflector 70 is made of a material whose reflectivity will not be degraded by a significant amount by wetting with materials used to provide an optical coupling between the light sensors and the optical window or between the optical window and the scintillator, such as optical greases, adhesives and potting compounds. Conventional reflective materials, such as porous teflon, lose their reflectivity in these situations. A preferred reflector is one whose reflectivity does not degrade by more than about 20% when wetted by the optical coupling material used at the interface where the reflector is installed (or when exposed to a potting material in general), and preferably one that does not degrade by more than about 10%. A particularly preferred reflector is a white polyester film, such as Lumirror™ polyester film sold by Toray Industries, Inc. previously sold for use as a reflector plate for LCD back-lighting applications."

FIG. 1 depicts components of a typical nuclear medical imaging system 100 (i.e., having a gamma camera or a scintillation camera) which includes a gantry 102 supporting one or more detectors 108 enclosed within a metal housing and movably supported proximate a patient 106 located on a patient support (e.g., pallet) 104. Typically, the positions of the detectors 108 can be changed to a variety of orientations to obtain images of a patient's body from various directions. In many instances, a data acquisition console 200 (e.g., with a user interface and/or display) is located proximate a patient during use for a technologist 107 to manipulate during data acquisition. In addition to the data acquisition console 200, images are often developed via a processing computer system which is operated at another image processing computer console including, e.g., an operator interface and a display, which may often be located in another room, to develop images. By way of example, the image acquisition data may, in some instances, be transmitted to the processing computer system after acquisition using the acquisition console.

More specifically, gamma cameras typically use a scintillating material such as, e.g., thallium iodide doped sodium iodide (NaI(TI)) to interact with gamma rays, creating photons, which must find their way out of the NaI(TI) and into a photomultiplier tube (PMT). Typically, there is at least one physical interface between the NaI(TI) and the PMT. Because the index of refraction of most scintillation crystals is substantially higher than 1.0, getting the scintillation light out of the crystal and into a PMT typically involves the use of an interface including an optical coupling medium.

This interface usually includes a material with an appropriate refractive index (RI) that will allow as many photons as possible to pass to the PMT, regardless of incident angle of the photon to the exiting surface of the NaI(TI). This material with an appropriate RI is typically a silicone-based material. Usually, silicone is chosen because of its RI and because of its stability over time. However, silicone-based materials have drawbacks that compromise the optics. For example, many silicone-based materials used are liquid-based "greases". These materials are typically very difficult to work with. They tend to migrate away from the area(s) where they are needed, and they tend to pick up contaminants and to discolor. Despite the drawbacks that these greases tend to pick up contaminants from the local environment and to discolor because of the absorbed contaminants, most gamma cameras use a silicone-based optical grease. Another drawback of these greases is that they also require extensive mechanical devices in order to hold the PMTs in the grease. In addition, these greases need to be replaced in the field relatively frequently (such as, e.g., about every 2-5 years) because of discoloration, which discoloration leads to signal degradation and to poor gamma camera performance. Accordingly, this discoloration causes the need for costly and time consuming on-site repairs. Most grease-based gamma cameras require a complete rebuild of its optics every 2-5 years due to these problems. As should be appreciated, this creates a significant amount of downtime for the facilities using these devices, which can be not only very time consuming, but very costly.

An alternative to these silicon-based greases has been the use of silicone-based "gels." These gels are "mechanically" much more forgiving than the above-noted greases. Among other things, these silicon-based gels are usually semi-solid and generally do not migrate. As a result, these gels can essentially act as a mechanical device to hold the PMTs in place. These gels will also tend to absorb less contamination than the greases. However, the present inventors have discovered that these silicone gels are still rather prone to discolor because of interactions of the platinum catalyst typically used in these gels with local contaminants (such as, e.g., outgassing epoxies from electronic components, coatings from parts within the gamma camera [e.g., organic coatings in contact with the gel], plasticizers from wiring inside the gamma camera and/or the like). Thus, as with silicon greases, the discoloration of silicon gels leads to degraded optics, which similarly triggers the need for on-site repairs and actions, and in severe cases can require a complete rebuilding of the gamma camera optics.

The present inventors have found that one noteworthy contaminant is the optical coating often used to help direct photons into the PMTs. This coating is typically placed onto the physical device (e.g., glass or plastic) that holds the PMTs. Because most PMTs have a geometry that does not allow 100% area coverage of the optical interface, some photons would be lost (e.g., in areas between the PMTs, leading to increased scan times or poorer images. Accordingly, this coating is typically used to reflect the photons back into an area that will allow them to be captured by a PMT for data processing.

While there has been some technical progress in striving to overcome some of the field repair problems, including the development of complex mathematical corrections to try to account for optical degradations, there remains a continued need for further improvements. Thus, while a variety of systems and methods are known, there remains a continued need for improved systems and methods overcoming the above and/or other problems with existing systems and methods.

SUMMARY OF THE PREFERRED EMBODIMENTS

The preferred embodiments of the present invention can significantly improve upon existing methods and/or apparatuses.

According to some preferred embodiments of the invention, a method of inhibiting discoloration of an optical coupling for a medical imaging system is performed that includes: inhibiting an interaction between an optical coating and an optical coupling that causes discoloration of the optical coupling. Preferably, the method further includes having the medical imaging system include a nuclear medical imaging system or a PET system. In preferred embodiments, the method further includes having the optical coupling between a scintillation crystal and a photomultiplier tube and the optical coating include a light reflective coating. In addition, the method preferably further includes having the optical coupling include an optical coupling gel, and, especially, a silicon-based coupling gel, and, more especially, an optical coupling gel including a platinum catalyst. In the most preferred implementations, the optical coating includes components selected from the group consisting of alkyds, polyesters and acrylics.

According to some other preferred embodiments, a method of inhibiting discoloration of an optical coupling for a medical imaging system is performed that includes: inhibiting platinum catalyst reactions that create light attenuating discoloration around a perimeter of at least one photo-detector.

According to some other preferred embodiments, a method of selecting an optical coating for a medical imaging system is performed that includes: selecting an optical coating based on at least the coating's i) optical properties and ii) potential for interacting with and discoloring an optical coupling in contact with the optical coating.

According to some other preferred embodiments, a method of upgrading or refurbishing a medical imaging system is performed that includes: providing a medical imaging system having an optical coating that is prone to cause discoloration of an adjacent optical coupling of the system; removing at least some of the optical coating and replacing it with an optical coating that is not prone to cause discoloration of the adjacent optical coupling of the system. In some embodiments, the removing and replacing is performed prior to any appreciable discoloration of the optical coupling occurs. In other embodiments, the removing and replacing is performed after an appreciable discoloration of the optical coupling occurs.

According to some other embodiments, a medical imaging system having stable camera optics is provided that includes: a photon emitting source that emits photons towards a plurality of photon receivers; an optical interface between the photon emitting source and the plurality of photon receivers; the optical interface including a lightguide and an optical coupling gel for directing photons into the photon receivers, and including a light reflective coating at locations adjacent the optical coupling gel and between the photon receivers; the optical coupling gel being prone to discoloration from local contaminants; and the light reflective coating having a chemistry that is free of contaminants that cause discoloration of the optical coupling gel. In preferred embodiments, the optical coupling gel includes a silicon-based coupling gel and the light reflective coating includes components selected from the group consisting of alkyds, polyesters and acrylics.

According to some other embodiments, a method for creating stable camera optics is performed that includes: emitting photons from a source towards a plurality of photon receivers; directing the emitted photons through an optical interface between the photon emitting source and the plurality of photon receivers, including directing the photons through a lightguide and an optical coupling gel and including reflecting photons off a light reflective coating at locations adjacent the optical coupling gel and between the photon receivers; and providing an optical coupling gel that is prone to discoloration from local contaminants, but providing the light reflective coating with a chemistry that is free of contaminants that cause discoloration of the optical coupling gel. In preferred embodiments, the method includes providing the optical coupling gel as a silicon-based coupling gel and the light reflective coating with components selected from the group consisting of alkyds, polyesters and acrylics.

According to some other preferred embodiments, a medical imaging system having stable camera optics is provided that includes: a photon emitting source that emits photons towards a plurality of photon receivers; an optical interface between the photon emitting source and the plurality of photon receivers including an optical coupling gel that is prone to discoloration from local contaminants and an optical coating adjacent the optical coupling gel; the optical coating having means for avoiding discoloration of the optical coupling gel.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention are shown by a way of example, and not limitation, in the accompanying figures, in which.

DETAILED DESCRIPTION OF THE PREFERRED EMBODIMENTS

Figure 1:
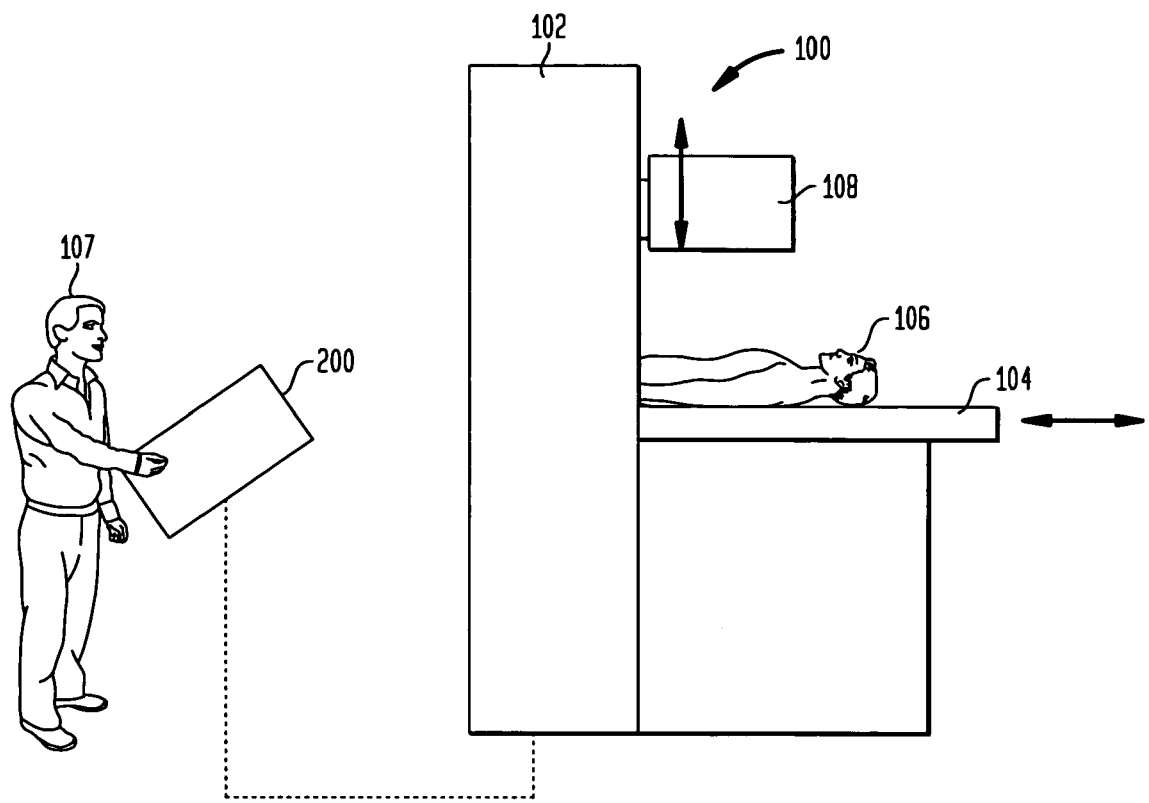
FIG. 1 is a schematic diagram of an illustrative nuclear medical imaging system within which some embodiments of the invention may be employed.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

According to the preferred embodiments of the invention, a system and method is provided for creating extremely stable optics that use optical coupling gels. Although coupling gels are prone to discoloration, the preferred embodiments enable the use of such gels without reducing their utility as an optical coupling agent, by, inter alia, creating an environment that will inhibit or prevent the optical coupling gels from changing color.

According to the preferred embodiments, a system and method is provided that controls certain chemistries, including, most preferably, the inhibition or prevention of undesirable platinum catalyst reactions that create colored compounds. Among other things, the preferred embodiments are very significant because they can inhibit or eliminate discoloration of preferred optical couplings (e.g., silicone gels). Among other things, by inhibiting or eliminating the discoloration of the preferred optical coupler, photon attenuation is substantially eliminated, allowing more photons to enter PMTs or the like in a given time. As a result, in the preferred embodiments, the signal will substantially not or will not degrade as a gamma camera or the like ages. Among other advantages, this substantial lack or complete lack of degradation means that extensive on-site repairs and/or the like actions that were previously required to remedy the attenuation can be virtually eliminated.

In the preferred embodiments, an optical coating is provided that will not cause the optical coupling gel to discolor as a result of contact therewith. The present inventors have discovered that historically optical coatings have generally been chosen substantially only because of their optical properties and their mechanical properties (e.g., toughness), without regard for the optical coating's potential for interaction with the optical coupling (e.g., a silicone gel) that will lead to discoloration. The present inventors have found that this prior methodology for selecting optical coatings has been problematic and has lead to significant gamma camera signal degradation, requiring extensive field work (e.g., repairs at a customer site or location).

In the preferred embodiments, an optical coating is provided that will not or that will substantially not react with a platinum-based catalyst or the like used in a silicone gel optical coupling. The present inventors have discovered that discoloration of the optical gel is caused by a reaction of a platinum-based catalyst with most optical coatings, leading to signal attenuation, and the need to perform extensive field actions to mitigate the problem. Thus, in the preferred embodiments, a methodology is provided that inhibits the reaction of a platinum-based catalyst with an optical coating that would result in the discoloration of the optical coupling.

In the preferred embodiments, the optical coupling includes silicon gels and, in the most preferred embodiments, silicon gels having a platinum catalyst. As described above, the preferred embodiments can inhibit or even eliminate the color generation caused by an interaction between the gel's platinum catalyst and the coatings that are in intimate contact with the gel. As a result, according to the preferred embodiments, users of gamma cameras or the like can operate their cameras for substantially longer periods of time (such as, e.g., for many years) without any required intervention to resolve such an optical degradation problem.

Figure 2:
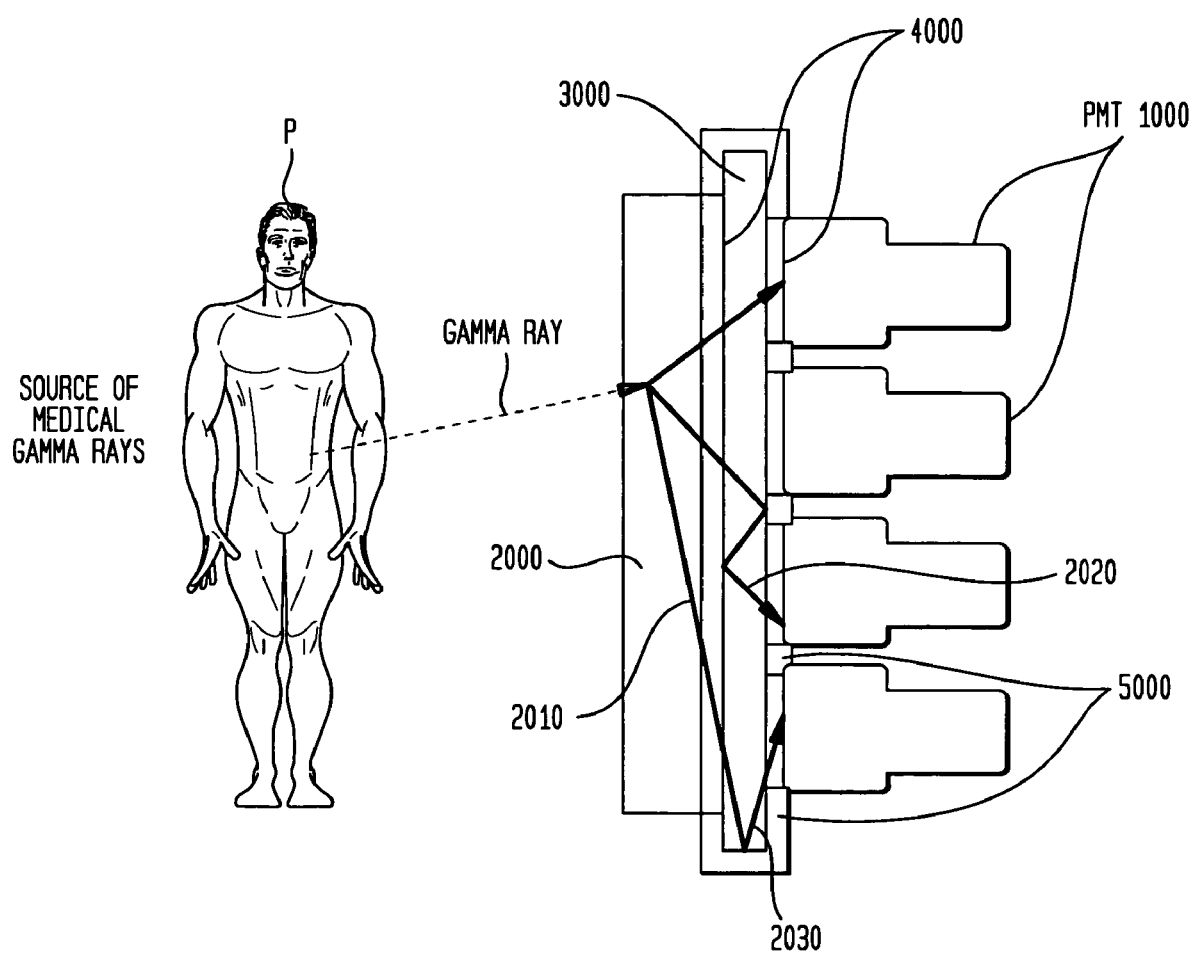
FIG. 2 is another schematic diagram depicting gamma event capture and relevant optical components in an illustrative nuclear medical imaging system within which some embodiments of the invention may be employed.

FIG. 2 shows an illustrative embodiment of the invention employed within the context of a gamma camera of a nuclear medical imaging apparatus. More specifically, FIG. 2 is a schematic diagram depicting an illustrative array of photomultiplier tubes 1000 separated from a crystal 2000 by a plexiglass lightguide or lightpipe 3000 with an optical coupling gel 4000 in between the PMT and the lightpipe and also in between the lightpipe and the crystal. In addition, other regions around the lightpipe are coated with a light reflective coating 5000 as shown to help ensure that the photons actually enter the PMTs.

In operation, the patient P is injected with a pharmaceutical that contains a radioactive material that decays to emit gamma rays. When a gamma ray hits the gamma camera at the NaI(TI) crystal, the gamma ray is converted into a set of photons. As shown, some of these photons 2010 travel from the NaI(TI) crystal through a first layer of optical coupling gel 4000, then through a light pipe 3000 (which can, e.g., be made of a plastic, such as, e.g., Plexiglas and/or the like), then through a second layer of optical coupling gel 4000, and finally into a photomultiplier tube (PMT). In operation, not all photons will necessarily end up in one of the PMTs. For example, some of the photons may be lost out of the light pipe. In order to limit the loss of photons from the light pipe, a reflective coating 5000 is located around the periphery of the light pipe to help direct photons into the PMTs. For example, as shown in FIG. 2, the reflective coating is preferably located in areas or regions outside of the light paths with the coupling gels, such as, e.g., in areas where there are no PMTs. In this manner, the reflective coating helps to redirect the photons 2010 so that they will end up in a PMT (such as, e.g., depicted by the illustrative reflected photon light paths 2020 and 2030 which pass through the first coupling gel, reflect off a reflective coating, reflect within the light pipe and enter into a respective PMT).

Figure 3:
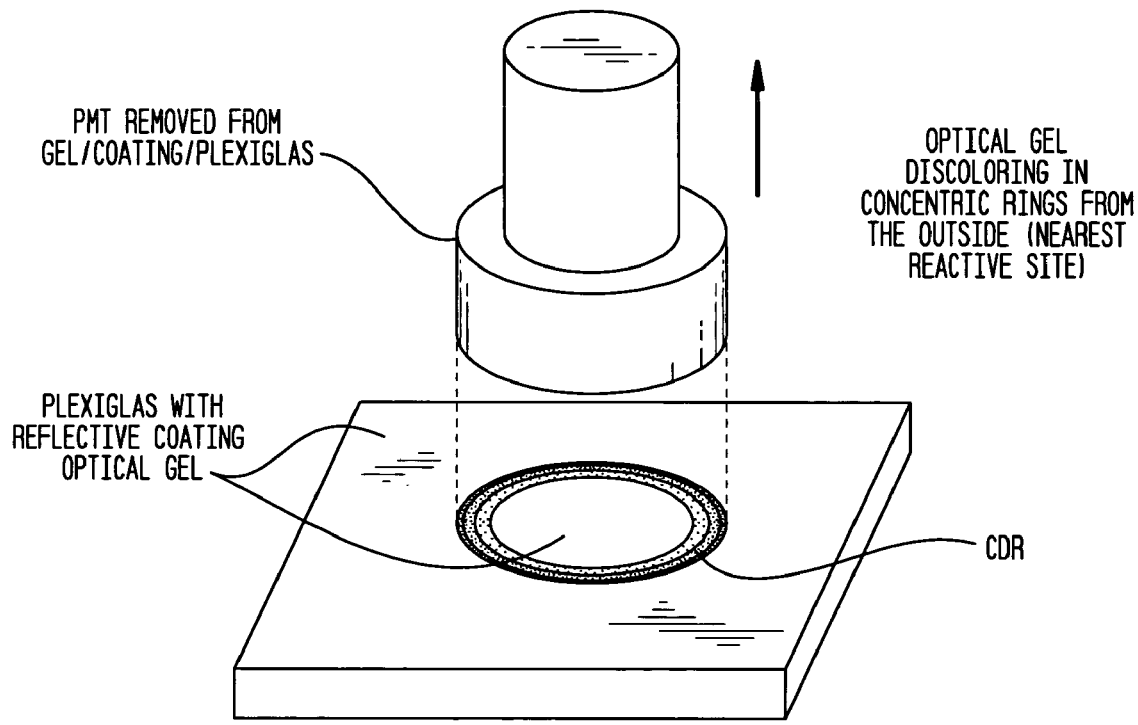
FIG. 3 is a schematic perspective view demonstrating optical coupling discoloration issues.
Figure 4:
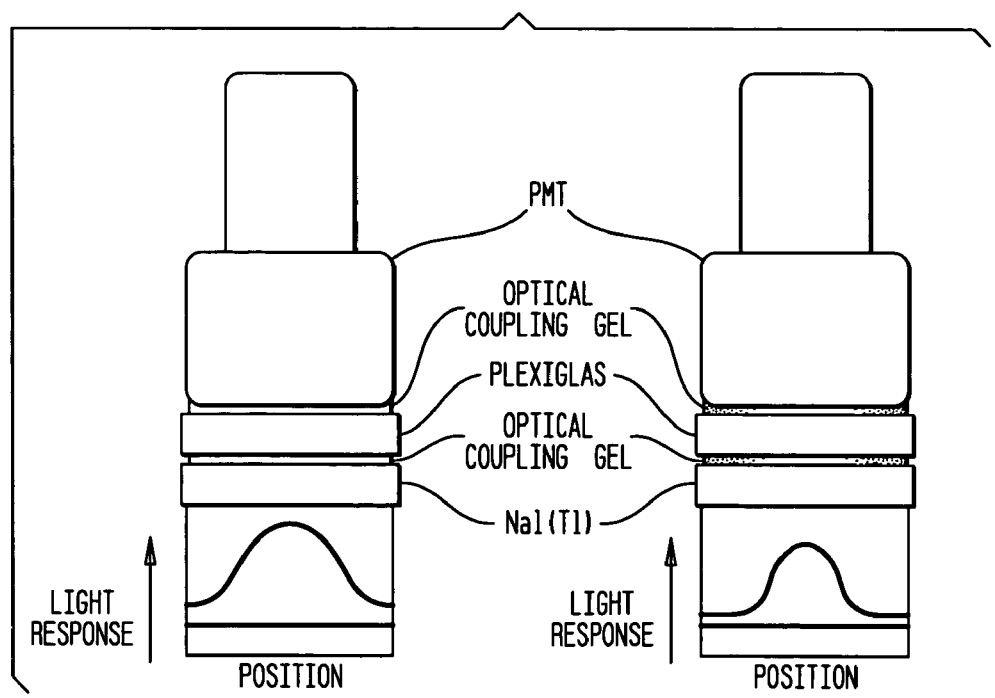
FIG. 4 is a schematic diagram showing light response as a function of incident light location in an assembly without optical coupling gel discoloration (left side) and in an assembly with optical coupling gel discoloration (right side).

As described above, prior to the present invention, the preferred optical coupling gels (i.e., silicone-based gels) would darken in areas where the coupling gel 4000 would contact conventional light reflective coatings 5000. In addition, when the coupling gel darkened, it would generally darken unevenly. For example, often the gel 4000 would darken a larger extent at locations closest to the points of contact with the optical coating 5000 and would darken a lesser extent as the distance from the points of contact increased from the coating 5000. For illustrative purposes, FIG. 3 demonstrates an illustrative varied color degradation region CDR around the periphery of a PMT. Among other things, this varied or uneven darkening can be particularly problematic for at least the following two reasons: 1) it decreases the amount of light that gets to the PMT as described above; and 2) it also significantly affects the Light Response Function (LRF) of the gamma camera. In this regard, the LRF is used in image correction processes. Typically, it involves the careful measurement of the LRF with a clean (i.e. non-discolored) gel. This LRF is then loaded into the gamma camera computer and used as part of the image correction processes. When the gel has a varied discoloration (such as, e.g., being or discolored or darker near the perimeter of the PMT verses closer to the interior as shown in FIG. 3), the LRF changes, but the computer stored values are not changed. Accordingly, this can result in a significantly less accurate image creation. By way of illustration, FIG. 4 is a schematic diagram depicting light responses as a function of incident light location for a first assembly (at the left) in which an optical coupling gel is free from discoloration and for a second assembly (at the right) in which an optical coupling gel is subject to discoloration, demonstrating a substantially light response attenuation due to discoloration.

In the preferred embodiments of the present invention, color development is greatly minimized by providing a coating chemistry that will not or that will substantially not react with the coupling gel, and, in particular, with a platinum complex within a silicone optical coupling gel. As a result, in the preferred embodiments, there will be significantly less color generation. Therefore, in applications such as, by way of example, similar to that shown in FIG. 2, there will be a significantly lower loss of photons and a significantly lower change in the LRF.

In the most preferred embodiments, a reflective coating will include a chemistry that inhibits, limits or prevents interaction or otherwise minimally reacts with or does not react with optical coupling gels, such as, e.g., in particular with silicon optical coupling gels, and especially silicon optical coupling gels having a platinum complex. In the most preferred embodiments, the coating chemistry includes alkyds, polyesters, acrylics and/or other chemistries that do not or that substantially do not tend to react with a platinum catalyzed silicone gel. In contrast, typical prior chemistries used for such reflective coatings included urethanes and epoxies, which were both particularly prone to causing the platinum catalyzed silicone gels to discolor.

While a variety of coating materials could be employed by those in the art based on this disclosure, in the preferred embodiments, one or more of the noted illustrative chemistries is employed. Of the noted illustrative chemistries that can be employed, acrylic coatings are the most preferred in some embodiments.

In some embodiments, such chemistries that do not or that substantial do not result in optical gel discoloration are used for substantially the entire or the entire content of the reflective coatings. In other embodiments, such chemistries are employed as a sufficient portion of these coatings to appreciably limit discoloration. In other embodiments, such chemistries are employed at least in regions of these coatings proximate to the optical coupling gel to appreciably limit discoloration. In yet some other embodiments, these chemistries or materials are employed as or within an intermediate layer in between the optical coupling gel and the optical coating. While in the most preferred embodiments, all or substantially all of the interfaces between an optical coating and an optical coupling gel are protected by chemistries in accordance with one or more embodiment of the invention as described herein, in some embodiments only some or a portion of the interfaces between an optical coating and an optical coupling gel may be protected by chemistries in accordance with one or more embodiment of the invention described herein.

In some preferred implementations, these chemistries or materials are employed within newly constructed medical imaging devices prior to transport to a consumer (such as, e.g., a medical facility) and/or prior to the initial use of such medical imaging devices by a consumer. In these contexts, these chemistries are, thus, preferably implemented within the medical imaging systems upon the initial manufacture and/or initial assembly thereof.

However, in some other preferred implementations, these chemistries or materials are employed within methods for upgrading and/or refurbishing existing systems. By way of example, in some embodiments, an existing system having an optical coating that is prone to causing discoloration of the coupling gels is upgrading to include chemistries or materials in accordance with the preferred embodiments of the invention. In some embodiments, the upgrading and/or refurbishing can be done prior to any level of or prior to any significant level of discoloration of a coupling gel. In addition, in some embodiments, the upgrading and/or refurbishing can be done once discoloration of a coupling gel has occurred and on-site action is desired or required. In some illustrative embodiments, upgrading and/or refurbishing can include the steps of 1) removing some or, more preferably, all of the existing coating and 2) replacing the existing coating with a new coating having chemistries or materials according to the preferred embodiments described herein. In some other embodiments, upgrading and/or refurbishing can include the step of providing new coating portions having chemistries or materials according to the preferred embodiments described herein in a manner to limit or prevent discoloration of the coupling gel (e.g., in some embodiments, such materials may be added to existing coatings or may be added between existing coatings and the coupling gels).

Accordingly, in the most preferred embodiments, conventional gamma cameras and/or other imaging devices can be greatly improved upon by upgrading and/or refurbishing coatings, such as, for example, to replace conventional coatings with coatings having chemistries or materials as described herein, such as, e.g., most preferably to employ an acrylic coating.

Among other things, the preferred embodiments can greatly enhance the quality of the imaging optics and the longevity of the imaging system (e.g., greatly increasing the time periods between needed on-site repairs, field actions and/or rebuilds of imaging system optics).

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure and during the prosecution of this case, the following abbreviated terminology may be employed: "e.g." which means "for example."

What is claimed is:

1. A method of inhibiting, in a nuclear medical imaging system, discoloration of a platinum-catalyzed silicone-based optical coupling for coupling a photomultiplier tube to a surface of a lightguide having a reflective coating with which the optical coupling makes contact, comprising:
   forming said reflective coating from a material that does not substantially react with a platinum catalyst of said optical coupling.

2. The method of claim 1, further including having said medical imaging system include a PET system.

3. The method of claim 1, further including having said optical coupling include an optical coupling gel.

4. The method of claim 1, further including having said reflective coating include components selected from the group consisting of alkyds, polyesters and acrylics.

5. The method of claim 4, further including having said reflective coating include an alkyd.

6. The method of claim 4, further including having said reflective coating include a polyester.

7. The method of claim 4, further including having said reflective coating include an acrylic.

8. A method of upgrading or refurbishing a medical imaging system having a reflective coating that is prone to cause discoloration of an adjacent platinum-catalyzed optical coupling of the system, comprising:
   removing at least some of said reflective coating and replacing it with a reflective coating that is formed of a material that is substantially non-reactive with a platinum catalyst of said optical coupling.

9. The method of claim 8, wherein said removing and replacing is performed prior to any appreciable discoloration of the optical coupling occurs.

10. The method of claim 8, wherein said removing and replacing is performed after an appreciable discoloration of the optical coupling occurs.

11. The method of claim 10, further including refurbishing the discolored optical coupling.

12. A medical imaging system having stable camera optics, comprising:
   a photon emitting source that emits photons towards a plurality of photon receivers;
   an optical interface between said photon emitting source and said plurality of photon receivers;
   said optical interface including a lightguide and a platinum-catalyzed optical coupling gel for directing photons into said photon receivers, and including a light reflective coating at locations adjacent to said optical coupling gel and between said photon receivers;
   said light reflective coating having a chemistry that inhibits platinum catalyst reactions with said optical coupling gel.

13. The system of claim 12, wherein said optical coupling gel includes a silicone-based coupling gel and said light reflective coating includes components selected from the group consisting of alkyds, polyesters and acrylics.

14. The system of claim 13, wherein said light reflective coating includes an alkyd.

15. The system of claim 13, wherein said light reflective coating includes a polyester.

16. The system of claim 13, wherein said light reflective coating includes an acrylic.

17. The system of claim 13, wherein said photon emitting source is a scintillation crystal and said photon receivers include an array of photomultiplier tubes.

18. A method of inhibiting discoloration of a platinum-catalyzed silicone-based optical coupling for coupling a photodetector to a scintillator of a medical imaging system, comprising:
   forming a reflective coating around at least a perimeter of a photodetector of a material that inhibits platinum catalyst reactions with said optical coupling that create light attenuating discoloration around said perimeter.

* * * * *